(12) United States Patent
Angeli et al.

(10) Patent No.: US 10,145,831 B2
(45) Date of Patent: *Dec. 4, 2018

(54) METHOD AND SYSTEM FOR HUMAN PRESENCE CORRELATION USING CARBON DIOXIDE

(71) Applicant: SRC, Inc., North Syracuse, NY (US)

(72) Inventors: Mark Angeli, West Chester, OH (US); John Durst, New York, NY (US); Garrett Liddil, Manlius, NY (US); Marcello M. DiStasio, Syracuse, NY (US)

(73) Assignee: SRC, Inc., North Syracuse, NY (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/293,665

(22) Filed: Oct. 14, 2016

(65) Prior Publication Data

US 2018/0106775 A1 Apr. 19, 2018

Related U.S. Application Data

(63) Continuation of application No. 13/804,065, filed on Mar. 14, 2013, now Pat. No. 9,470,670.

(51) Int. Cl.
*G01N 31/00* (2006.01)
*G01N 33/00* (2006.01)
*G01V 11/00* (2006.01)

(52) U.S. Cl.
CPC ....... *G01N 33/0067* (2013.01); *G01V 11/002* (2013.01); *G01N 2033/0068* (2013.01)

(58) Field of Classification Search
CPC .......... G01N 33/0067; G01N 33/0037; G01N 33/004; G08B 21/14; G08B 21/22
USPC ....................................... 702/22–24
See application file for complete search history.

(56) References Cited

U.S. PATENT DOCUMENTS

| | | | |
|---|---|---|---|
| 6,344,798 B1 | 2/2002 | Schell | |
| 6,424,267 B1 | 7/2002 | Schell | |
| 7,394,349 B2 * | 7/2008 | Marek | G08B 21/22 180/271 |
| 9,227,484 B1 * | 1/2016 | Justice | B60N 2/002 |
| 9,470,670 B2 * | 10/2016 | Angeli | G01N 33/0067 |
| 2014/0269384 A1 * | 9/2014 | DiStasio | G01S 13/888 370/252 |

OTHER PUBLICATIONS

Murphy, J., Using CO2 for Demand-Controlled Ventilation, http://www.trane.com/Commercial/library/vol31_3, Engineers Newsletter, 2002, vol. No. 3, pp. 1-10.

(Continued)

*Primary Examiner* — An Do
(74) *Attorney, Agent, or Firm* — Bond Schoeneck & King, PLLC; George McGuire

(57) ABSTRACT

Method and system for detecting and/or quantifying recent human presence in an environment using a calculated rate of decay of carbon dioxide concentration levels within that environment. A sensor measures the change in carbon dioxide levels over time to calculate the rate of decay to equilibrium and extrapolate recent human presence. Also provided is a method and system for quantifying recent human activity in an environment using the calculated rate of decay to equilibrium.

20 Claims, 3 Drawing Sheets

(56) References Cited

OTHER PUBLICATIONS

Dwyer, Duct Mount Carbon Dioxide Transmitter, http://www.dwyer-inst.co.uk/Products/Product.cfm?Group_ID=20025, NDIR Sensing Technology, 2000 PPM Range, p. 1, as of Sep. 2009.
Honeywell, The CO2 Sensor Family Expands!, http://www.honeywell.com, 63-8598 11/00 BN/RC/PC p. 1, as of Nov. 2000.
Singh, H. et al., Predictions of Indoor CO2 Concentration Levels in Four UK School Buildings with Three Ventilation Scenarios, Warwick Institute of Sustainable Energy and Resources, University of Warwick, UK, 5th International Conference, Improving Energy Efficiency in Commercial Buildings (IEECB'08), Frankfurt, Apr. 10-11, 2008, pp. 1-8.
Federspiel, C., Estimating the Inputs of Gas Transport Processes in Buildings, IEEE Transactions on Control Systems Technology, vol. 5, No. 5, Sep. 1997, pp. 480-489.
Persily, A.K., The Relationship Between Indoor Air Quality and Carbon Dioxide, Building and Fire Research Laboratory, National Institute of Standards and Technology, USA, pp. 1-6, 1996.
Jankovic, J.T. et al., Occupant Generated Carbon Dioxide as a Measure of Dilution Ventilation Efficiency, PubMed, http://www.ncbi.nlm.nih.gov/pubmed/8765206, Am Ind Hyg Assoc J., Aug. 1996; 57(8):756-9.
Aglan, H., Predictive Model for CO2 Generation and Decay in Building Envelopes, American Institute of Physics, Journal of Applied Physics, vol. 93, No. 2, Jan. 15, 2003, pp. 1287-1290.
Lam, K. et al., Occupancy Detection through an Extensive Environmental Sensor Network in an Open-Plan Office Building, Building Simulation 2009, Jul. 2009, pp. 1452-1459.
Manewatana, T., Measurement and Prediction of Carbon Dioxide in an Office Building, ASHRAE Journal, May 2003, pp. 8-12.
Emmerich, S. et al., State-of-the-Art Review of CO2 Demand Controlled Ventilation Technology and Application, National Institute of Standards and Technology, Mar. 2001, pp. 1-43.
Leephakpreeda, R. et al., Occupancy-Based Control of Indoor Air Ventilation: A Theoretical and Experimental Study, ScienceAsia 27, 2001, pp. 279-284.
Wang, S. et al., Experimental Validation of CO2-Based Occupancy Detection for Demand-Controlled Ventilation, Sage, http://ibe.sagepub.com/cgi/content/abstract/8/6/377, Indoor Built Environ 1999;8:377-391.
Wang, S. et al., CO2-Based Occupancy Detection for On-Line Outdoor Air Flow Control, Karger, http://content.karger.com/ProdukteDB/produkte.asp?Aktion=ShowPDF&ProduktNr=224157&Ausgabe=226062&ArtikelNr=24577, Indoor Build Envirn 1998;7:165-181.
Ke, Y. et al., Using Carbon Dioxide Measurements to Determine Occupancy for Ventilation Controls, http://www2.nkfust.edu.tw/~ypke/abstract.html, ASHRAE Transactions, vol. 103, pt. 2, pp. 365-374, 1997.

* cited by examiner

METHOD AND SYSTEM FOR HUMAN PRESENCE CORRELATION USING CARBON DIOXIDE

CROSS-REFERENCE TO RELATED APPLICATIONS

This application is a continuation of and claims priority to U.S. patent application Ser. No. 13/804,065, filed Mar. 14, 2013 and now allowed (issuing Oct. 18, 2016 as U.S. Pat. No. 9,470,670), entitled "Method and System for Human Presence Correlation Using Carbon Dioxide," the entire contents of which are incorporated herein by reference in its entirety.

BACKGROUND OF THE INVENTION

1. Field of the Invention

The present invention relates to the detection of recent human presence, and, more specifically, to a method for detecting recent human presence in an environment using the rate of decay of carbon dioxide concentration levels within that environment.

2. Description of the Related Art

Real-time detection of human presence in an environment such as a home, car, or office can be advantageous for several reasons. Indeed, there are many systems that detect human presence in real-time, including lighting and ventilation systems, in order to reduce energy consumption and costs or to improve the quality of the air within the space. These systems use a variety of means to detect human presence in real-time, including sensor technologies such as gas concentration sensors, infrared detectors, seismic detectors, and other human presence detectors. In limited applications, these systems can also quantify the real-time human presence by determining the number of humans that are present in a space.

However, these systems are not capable of either detecting recent human presence once the space no longer has a human present or quantifying recent human presence once the space no longer has a human present. Once the environment or space is empty the sensor is no longer activated and is thus unable to determine human presence. Further, these systems are not able to function in a space or environment that is not already configured to contain a sensor. In other words, the human presence cannot be detected unless the sensor was in the room at the same time as the human beings.

However, human presence will typically leave behind signatures that can be detected and analyzed. Additionally, measurements of some signatures can be quantitative such that the amount of recent human presence can be determined. Thus, there is a need for methods and systems that detect and/or quantify recent human presence.

BRIEF SUMMARY

It is therefore a principal object and advantage of the present invention to provide a method and system for detecting and/or quantifying recent human presence in an environment or space.

It is another object and advantage of the present invention to provide a method and system for detecting and/or quantifying recent human presence in a space using carbon dioxide concentration levels.

It is yet another object and advantage of the present invention to provide a method and system for detecting and/or quantifying recent human presence in a space using a calculated rate of decay of decay carbon dioxide concentration levels.

Other objects and advantages of the present invention will in part be obvious, and in part appear hereinafter.

In accordance with the foregoing objects and advantages, the present invention provides a method for detecting recent human presence in a space. The method comprises the steps of: (i) measuring the concentration of carbon dioxide within the space to obtain a first carbon dioxide measurement; (ii) measuring the concentration of carbon dioxide within the space after a first period of time has elapsed in order to obtain a second carbon dioxide measurement; (iii) optionally obtaining additional carbon dioxide measurements; (iv) calculating the carbon dioxide rate of decay using the second carbon dioxide measurements; (v) accepting a carbon dioxide concentration of interest; (vi) extrapolating the time at which the concentration of carbon dioxide in the space was approximately equivalent to the carbon dioxide concentration of interest; and (vii) correlating the carbon dioxide rate of decay to a level of human presence in the space at the extrapolated times for a set of candidate occupancy/time of departure pairs.

A second aspect of the present invention provides a system for detecting recent human presence in a space. The system comprises: (i) measuring means configured to measure the concentration of carbon dioxide within the space to obtain a first carbon dioxide measurement and configured to measure the concentration of carbon dioxide within the space after a first period of time elapses in order to obtain a second carbon dioxide measurement; (iii) calculating means configured to calculate the carbon dioxide rate of decay using the carbon dioxide measurements; (iv) accepting means configured to accept a carbon dioxide concentration of interest; (v) extrapolating means configured to extrapolate the time at which the concentration of carbon dioxide in the space was approximately equivalent to the carbon dioxide concentration of interest; and (vi) correlating means configured to correlate the carbon dioxide rate of decay to a level of human presence in the space at the extrapolated times for a set of candidate occupancy/time of departure pairs.

A third aspect of the present invention provides a computer program stored on a computer useable storage medium. The computer program is configured to implement a method for detecting recent human presence in a space, the method comprising the steps of: (i) measuring the concentration of carbon dioxide within the space to obtain a first carbon dioxide measurement; (ii) measuring the concentration of carbon dioxide within the space after a first period of time elapses in order to obtain a second carbon dioxide measurement; (iii) optionally obtaining additional carbon dioxide measurements; (iv) calculating the carbon dioxide rate of decay using the carbon dioxide measurements; (v) accepting a carbon dioxide concentration of interest; (vi) extrapolating the time at which the concentration of carbon dioxide in the space was approximately equivalent to the carbon dioxide concentration of interest; and (vii) correlating the carbon dioxide rate of decay to a level of human presence in the space at the extrapolated times for a set of candidate occupancy/time of departure pairs.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION

Figure 1:
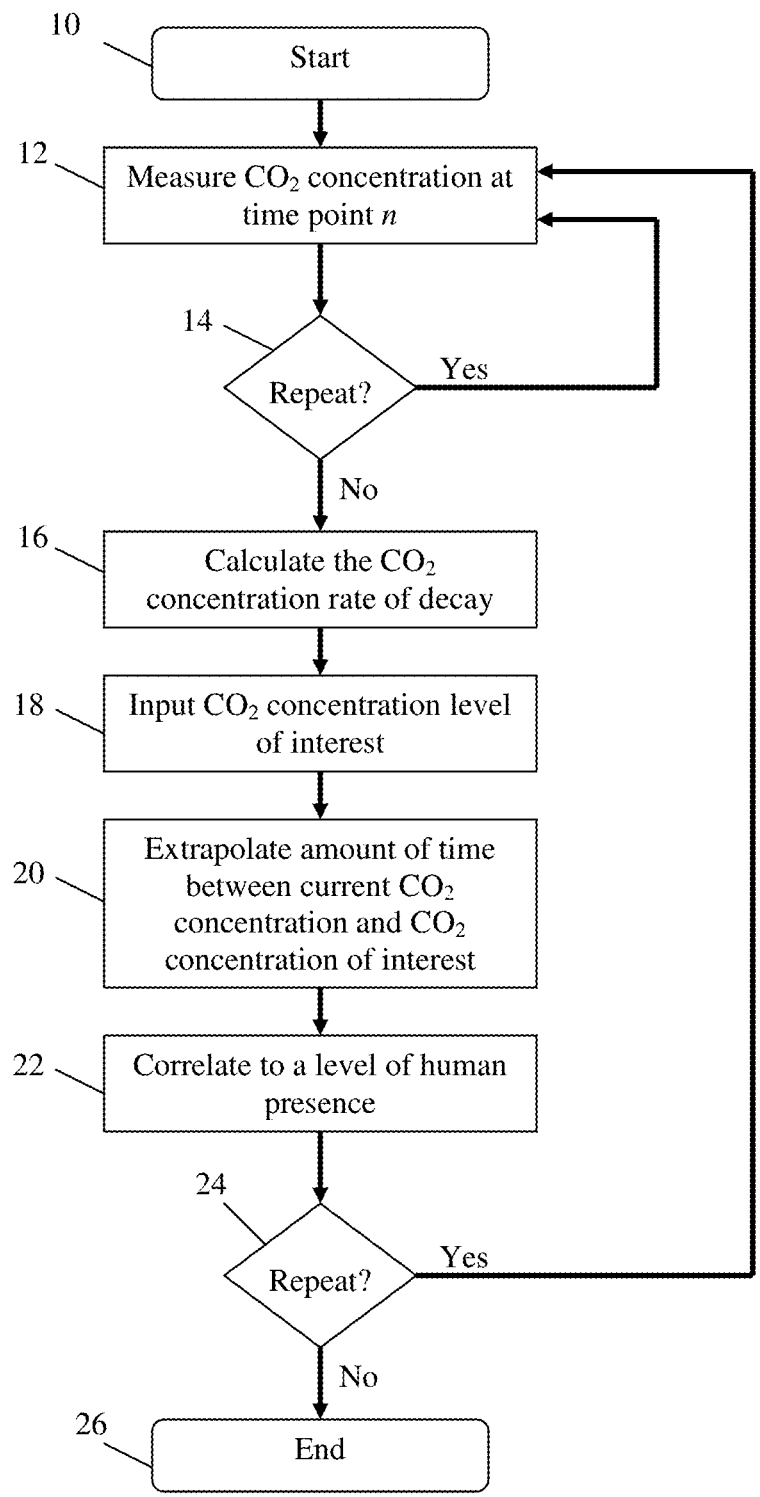
FIG. 1 is a flowchart of the human detection method according to an embodiment.

Referring now to the drawings, wherein like reference numerals refer to like parts throughout, there is seen in FIG. 1 a flowchart of the human detection method according to one embodiment of the present invention.

The process begins at step 10 in some defined space 100 (not shown). Space 100 can be any partially or completely enclosed environment such as a car, room, house, office, building, or any other structure or natural space capable of sustaining a temporary rise in carbon dioxide ("$CO_2$") levels in response to human presence. Preferably defined space 100 has recently contained one or more human beings, especially at some point within the previous 2 hours. However, since the goal of the systems and methods described herein is to determine whether one or more human beings were recently within space 100, it is not necessary that the space contain recent human activity.

At step 12, the initial concentration of $CO_2$ in space 100 is measured. There are many different methods and systems for measuring the amount of $CO_2$ in the air, although the two most common are infrared gas sensors and chemical gas sensors. Infrared gas sensors operate under the principle that $CO_2$ absorbs a specific wavelength of the electromagnetic spectrum. The sensor measures the amount of that specific wavelength which is absorbed, and this amount is proportional to the concentration of the gas.

Proceeding to step 14, additional $CO_2$ measurements are optionally obtained at one or more further time points. In a preferred embodiment the system measures the concentration of $CO_2$ in space 100 using at least two different time points; the initial concentration at time point 0 and then the concentration at some later time point, with further measurements being optional. At some length of time after human activity in space 100 has ceased, the concentration of $CO_2$ in the space will reach equilibrium and continued time points will likely not be useful.

The gas concentration measurements can optionally be formatted or otherwise adjusted to be received by an analysis algorithm. Once two or more gas concentration measurements are obtained by the sensor over time, the algorithm calculates the rate of decay of the $CO_2$ concentration, as shown in step 16 of the flowchart in FIG. 1. The decay rate is the temporal reduction of the carbon dioxide concentration at a given sampling point in space and is assumed to follow a first order exponential decay law:

$$C(t) = C_0 \cdot e^{-kt}$$

where N(t) is the concentration of $CO_2$ at time t. Sampling the $CO_2$ concentration at different time points will allow an estimation of the decay parameter k. So, for example, if there is a measurement at time $t_1$ and at a later point there is a measurement at time $t_2$:

$$C(t_1) = C_0 \cdot e^{-kt_1}$$

$$C(t_2) = C_0 \cdot e^{-kt_2}$$

Now, taking the natural log of these:

$$\ln(C(t_1)) = \ln(C_0) - k \cdot t_1$$

$$\ln(C(t_2)) = \ln(C_0) - k \cdot t_2$$

And then take the difference of the two to get:

$$\ln(C(t_2)) - \ln(C(t_1)) = -k \cdot (t_2 - t_1)$$

$$k = \frac{\ln(C(t_2)) - \ln(C(t_1))}{(t_2 - t_1)}$$

Accordingly, with just two measurements there is an estimate of the rate of decay of the $CO_2$ level (k). In the case where more than two measurements are taken, a more optimal regression method such as a least squares fit can be employed. According to one embodiment, predictions and/or inferences are made regarding the $CO_2$ concentration at an earlier time by use of a simple linear regression model based on our decay estimate and our measurements.

For a given enclosed area, the $CO_2$ concentration level is associated with the number of people present at a given time, and the mapping between the number of people, the enclosed area volume and $CO_2$ concentration level is established as prior calibration/reference information. This reference information together with the measurement and the estimated model parameters (e.g. $CO_2$ decay rate, k) then enables the system to automatically infer and present a prior occupancy/time profile. The reference information also provides the user with a set of suggested $CO_2$ levels corresponding to given potential human occupancy numbers. The user can use this information to specify $CO_2$ levels of interest for systems prediction.

Figure 3:
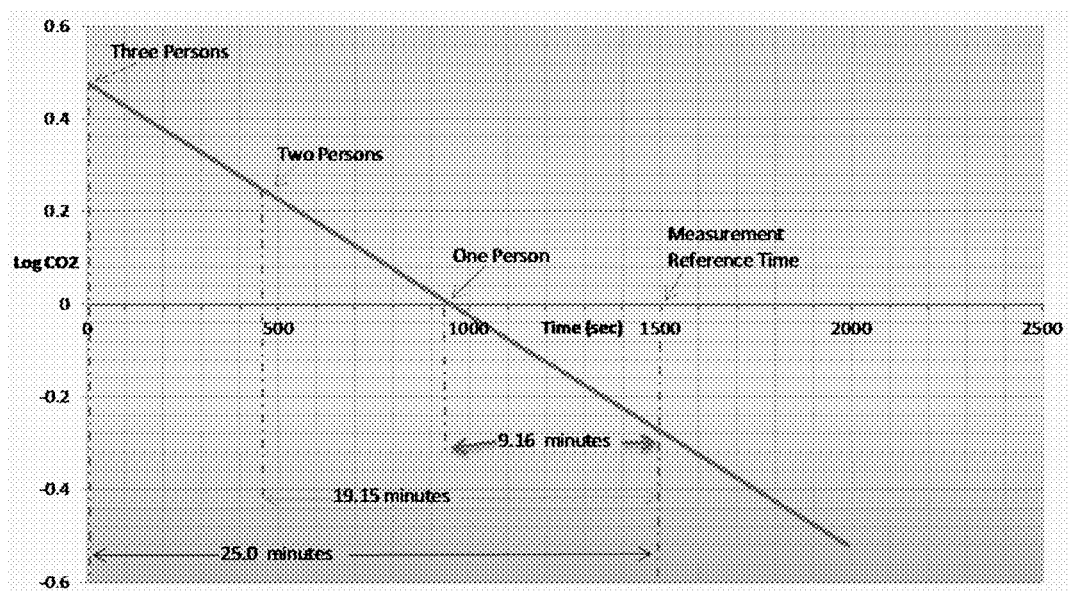
FIG. 3 is an example plot of a calculation used for determining occupancy numbers and/or departure times for an exemplar measurement set, according to an embodiment.

At step 18, the system generates a multi-hypothesis occupancy/time profile which consists of a set of possible occupancy numbers and associated time since exit, according to one embodiment. The system estimates these by solution of the following time estimate equation:

$$T_j = \frac{\ln(C_j) - \ln(C(t_{ref}))}{k}$$

where $T_j$ is the time since the number of people ($N_j$) left the space of interest. This step may not require any input from the user, since the reference $CO_2$ level, $C(t_{ref})$ can be selected from the measurement set either automatically or by the user, and the decay rate can be estimated as discussed above. The conversion from the $CO_2$ concentration level to the occupancy number ($N_j$) is effected via, for example, a priori reference tables. The reference tables provide the mapping from $CO_2$ level to an occupancy level estimate. The reference tables can be constructed, for example, for a set of enclosed area templates, e.g. 8'×10' room or 20'×40' space, and many other variations are possible. An example of an occupancy—"time since departure" chart from a calculation using the above equation and the associated table is given by FIG. 3 and Table 1, respectively. Note the $CO_2$ values, occupancy numbers and associated times are for example only.

TABLE 1

| $CO_2$ Level (Predicted) | Number of Occupants | Time Since Departure |
|---|---|---|
| 0.47 | 1 | 9.16 |
| 0.72 | 2 | 19.15 |
| 1.13 | 3 | 25 |

In step 22, the analysis algorithm extrapolates the amount of time that has elapsed since space 100 contained the $CO_2$ concentration of interest. With that information, the analysis algorithm can correlate the $CO_2$ concentration of interest and the amount of time to the level of human activity. In one embodiment, the analysis algorithm takes into consideration the size and/or volume of space 100 when performing one or more of the above calculations. The level of human activity can include the number of people that are predicted to have occupied space 100. In one embodiment, the level of human activity is determined from the related functions of the number of people in the space as well as the physical activity of the people in that space. For example, people who are performing a sedentary activity such as sitting, standing, or conversing typically produce less $CO_2$—and therefore cause lower $CO_2$ levels—than people who are physically active. Therefore, a certain $CO_2$ level determined by the method and system described herein may indicate a number N of sedentary people who recently occupied space 100, while that same level may indicate a number X of physically active people who recently occupied space 100, where X<N. The level of human activity can be preset or automatically determined by algorithm or device, or can be input or selected by the user depending upon a variety of factors including prior information, the size of the space, the typical use of the space, and other factors.

In step 24, the user and/or the algorithm can decide whether to obtain further $CO_2$ measurements. Additional $CO_2$ measurements can be used, for example, to further refine the results of the initial analysis. If further measurements are to be obtained, the system returns to a previous step such as step 12. If no further measurements are to be obtained, the method ends at step 26.

Figure 2:
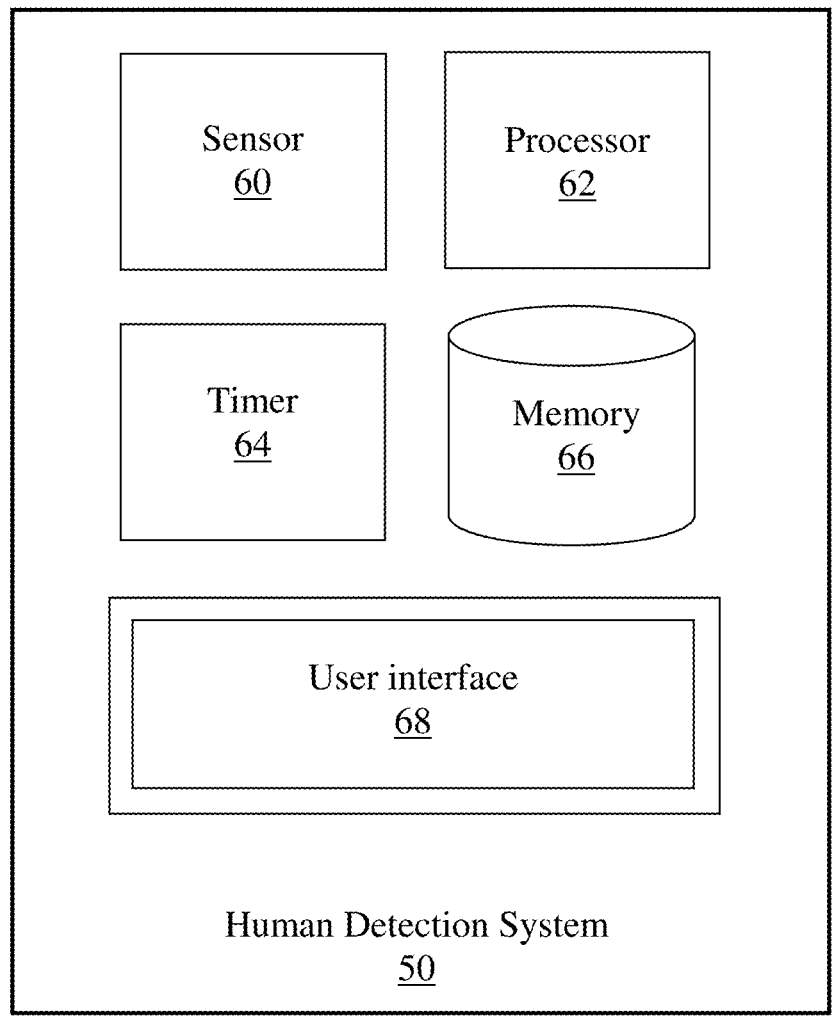
FIG. 2 is a component schematic of a human detection system according to an embodiment.

FIG. 2 is a component schematic of a human detection system 50 according to one embodiment of the invention. The system includes a sensor module 60, which is configured to measure the concentration of $CO_2$ in space 100. There are many different methods and systems for measuring the amount of $CO_2$ in the air, although the two most common are infrared gas sensors and chemical gas sensors. The module can alternatively include any known method of $CO_2$ measurement known to those skilled in the art.

After an initial $CO_2$ measurement is obtained, additional $CO_2$ measurements are optionally obtained at one or more further time points. In a preferred embodiment the system measures the concentration of $CO_2$ in space 100 using at least two different time points; the initial concentration at time point 0 and then the concentration at some later time point, with further measurements being optional. The process of obtaining multiple timed $CO_2$ measurements can be fully automated within human detection system 50, or can be determined by the user. In an automated embodiment, system 50 contains a timer module 64 that causes the system to pause for a specific amount of time—either fixed or variable—between two or more $CO_2$ measurements. Timer module 64 can be any method of electronic timing known in the art, including electronic circuits, capacitors, relay switches, mechanical timers, electromechanical timers, or digital counters, among others. According to this embodiment, the signal to obtain the initial $CO_2$ measurement begins a series of two or more measurements that are spaced apart in time by the timer. To accomplish this, timer module 64 must be configured to regulate sensor 60. In another embodiment, the user sets the interval of time using a user interface, a button, a knob, or some other means of interaction with the timer module.

The system further includes a processor 62. The processor can be any means, mechanism, or method known in the art to perform one or more operations, including an electronic chip. The processor executes a computer code which embodies an analysis algorithm. In a preferred embodiment, the computer code is stored on a non-transitory storage medium, as shown by memory 66 in FIG. 2, which can also be configured to store one or more $CO_2$ measurements as well as the output of the analysis algorithm, other variables of space 100, and/or other input from the user.

Processor 62 receives input from sensor 60 and/or memory 66, and optionally from the user interface 68. Using that input the processor can calculate the rate of decay of the $CO_2$ concentration, the amount of time between a current $CO_2$ concentration and a previous $CO_2$ concentration, and/or the level of human presence or activity in space 100 at a previous time, among other outputs.

According to one embodiment of the present invention the gas sensor and the storage medium containing the computer code which embodies the analysis algorithm are components of a single device. In a preferred embodiment the device is a hand-held device which can be quickly and easily transported from one location to another. In this embodiment, gas measurements can be either captured in a format that can be used by the analysis algorithm, or can be automatically converted to a useable format for the algorithm.

In another embodiment only one or a few components of the device, such as the gas sensor, are transportable or enter space 100. In this embodiment, gas measurements can be stored in memory within the device for later analysis or can be wirelessly transmitted to another physical location for storage or immediate analysis by the algorithm. The other physical location can be nearby or can be thousands of miles away, including in space.

The flowchart in FIG. 1 illustrates the operation of the systems and methods according to several embodiments of the present invention. However, it should be noted that the blocks—which represent a step of function of the method or system—can be completed in an order that is not represented in the figure. For example, the systems or methods can be completed by skipping one or more blocks, adding other blocks, or changing the order of the blocks. The flowchart is meant to provide an exemplary embodiment of the present invention and is therefore not intended to limit the scope of the invention.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

Although the present invention has been described in connection with a preferred embodiment, it should be understood that modifications, alterations, and additions can be made to the invention without departing from the scope of the invention as defined by the claims.

What is claimed is:

1. A method for detecting recent human presence in a space, the method comprising the steps of:
    measuring, using a carbon dioxide sensor, the concentration of carbon dioxide within the space to obtain a first carbon dioxide measurement;

measuring, using a carbon dioxide sensor, the concentration of carbon dioxide within the space after a first period of time elapses to obtain at least a second carbon dioxide measurement;

calculating the carbon dioxide rate of decay using at least the first and second carbon dioxide measurements;

extrapolating, using the calculated rate of decay, the time at which the concentration of carbon dioxide in the space was approximately equivalent to a carbon dioxide concentration of interest; and correlating the carbon dioxide rate of decay to a level of human presence in the space at the extrapolated time.

2. The method of claim 1, wherein the space is a room.

3. The method of claim 1, wherein the carbon dioxide concentration of interest is predetermined by a user.

4. The method of claim 1, wherein the carbon dioxide sensor is an infrared gas sensor.

5. The method of claim 1, wherein the carbon dioxide sensor is a chemical gas sensor.

6. The method of claim 1, further comprising the step of estimating, based on the calculated rate of decay, a number of occupants of the space at the extrapolated time.

7. The method of claim 1, further comprising the step of receiving, from a user, an estimate of a number of occupants of the space at the extrapolated time, and further wherein said correlating step is based at least in part on the received number of occupants.

8. A system for detecting recent human presence in a space, the system comprising:

a sensor configured to measure the concentration of carbon dioxide within the space to obtain a first carbon dioxide measurement and configured to measure the concentration of carbon dioxide within the space after a first period of time elapses to obtain at least a second carbon dioxide measurement; and a processor configured to: (i) calculate the carbon dioxide rate of decay using at least the first and second carbon dioxide measurements; (ii) extrapolate, using the calculated rate of decay, the time at which the concentration of carbon dioxide in the space was approximately equivalent to a carbon dioxide concentration of interest; and (iii) correlate the carbon dioxide rate of decay to a level of human presence in the space at the extrapolated time.

9. The system of claim 8, wherein the sensor is an infrared gas sensor.

10. The system of claim 8, wherein the carbon dioxide sensor is a chemical gas sensor.

11. The system of claim 8, wherein the carbon dioxide concentration of interest is predetermined by a user.

12. The system of claim 8, further comprising a user interface.

13. The system of claim 8, wherein the processor is further configured to estimate, based on the calculated rate of decay, a number of occupants of the space at the extrapolated time.

14. The system of claim 8, wherein the processor is further configured to receive an estimate of a number of occupants of the space at the extrapolated time, and further wherein said correlation is based at least in part on the received number of occupants.

15. A computer program stored on a computer useable storage medium, the computer program configured to implement a method for detecting recent human presence in a space, the method comprising the steps of:

receiving, from a sensor, the concentration of carbon dioxide within the space to obtain a first carbon dioxide measurement;

receiving, from a sensor, the concentration of carbon dioxide within the space after a first period of time elapses to obtain at least a second carbon dioxide measurement;

calculating the carbon dioxide rate of decay using at least the first and second carbon dioxide measurements;

extrapolating, using the calculated rate of decay, the time at which the concentration of carbon dioxide in the space was approximately equivalent to a carbon dioxide concentration of interest; and correlating the carbon dioxide rate of decay to a level of human presence in the space at the extrapolated time.

16. The computer program of claim 15, wherein said space is a room.

17. The computer program of claim 15, wherein said carbon dioxide concentration of interest is determined by a user.

18. The computer program of claim 15, wherein the sensor is an infrared gas sensor.

19. The computer program of claim 15, wherein the carbon dioxide sensor is a chemical gas sensor.

20. The computer program of claim 15, further comprising the step of estimating, based on the calculated rate of decay, a number of occupants of the space at the extrapolated time.

* * * * *